United States Patent [19]

Duffy

[11] Patent Number: 5,053,019

[45] Date of Patent: Oct. 1, 1991

[54] INJECTION DEVICE

[75] Inventor: George J. Duffy, Foxrock, Ireland

[73] Assignee: Institute for Industrial Research and Standards, Dublin, Ireland

[21] Appl. No.: 540,404

[22] Filed: Jun. 19, 1990

Related U.S. Application Data

[60] Continuation of Ser. No. 210,272, Jun. 23, 1988, abandoned, which is a division of Ser. No. 032,697, Apr. 1, 1987, Pat. No. 4,767,415, which is a continuation of Ser. No. 706,423, Feb. 27, 1985, abandoned.

[30] Foreign Application Priority Data

Mar. 2, 1984 [IE] Ireland .................................. 504/84
Jan. 30, 1985 [IE] Ireland .................................. 216/85

[51] Int. Cl.⁵ .............................................. A61M 5/18
[52] U.S. Cl. ................................ 604/232; 128/655; 600/4
[58] Field of Search .................. 600/1, 3, 5; 128/654, 128/655, 659, 200.21; 604/21, 56, 82, 83, 113, 187, 191, 232

[56] References Cited

U.S. PATENT DOCUMENTS

| | | | |
|---|---|---|---|
| 1,948,388 | 2/1934 | Liberson | 604/191 |
| 2,515,956 | 7/1950 | Greenberg | 604/207 |
| 2,647,514 | 8/1953 | Ellis | 604/113 |
| 2,711,734 | 6/1955 | Moe | 604/159 |
| 2,939,459 | 6/1960 | Lazarte | 604/191 |
| 3,673,411 | 6/1972 | Glasser | 600/5 |
| 3,746,216 | 7/1973 | Frederick | 604/141 |
| 3,749,084 | 7/1973 | Cucchiara | 604/191 |
| 4,044,758 | 8/1977 | Patel | 604/191 |
| 4,122,836 | 10/1978 | Burnett | 604/187 |
| 4,190,046 | 2/1980 | Virag | 128/200.21 |
| 4,241,728 | 12/1980 | Mirell | 600/5 |

FOREIGN PATENT DOCUMENTS

1815118 6/1970 Fed. Rep. of Germany ........ 604/82
1054173 10/1953 France .

Primary Examiner—David Shay
Attorney, Agent, or Firm—Sughrue, Mion, Zinn, Macpeak & Seas

[57] ABSTRACT

A device for storing a discrete quantity of liquid for use in a primary medical syringe for a bolus injection. The device comprises a body member having a core member inserted in the reservoir of the primary syringe. A liquid passageway for storing a radionuclide for the bolus injection is formed by a helical groove around the core member. A secondary syringe may be included in the primary syringe to measure small quantities of injectate.

9 Claims, 7 Drawing Sheets

INJECTION DEVICE

This is a Continuation of Application No. 07/210,272 filed June 23, 1988, now abandoned which is a Division of Application U.S. Pat. No. 032,697 filed Apr. 1, 1987, and now U.S. Pat. No. 4,767,415, which is a continuation of Application No. 06/706,423 filed Feb. 27, 1985, and now abandoned.

FIELD OF THE INVENTION

The present invention relates to a device for storing a discrete quantity of liquid for use with a medical syringe, the device being of the type having a chamber to store the liquid, and a pair of communicating means communicating respectively between the chamber and the syringe reservoir, and the chamber and a needle.

BACKGROUND TO THE INVENTION

In many cases, it is important to be able to inject intravenously a discrete quantity of liquid rapidly into a patient. It is also important that mixing of the discrete quantity of liquid with the patient's blood and/or a driving liquid, should be kept to a minimum. For example, certain drugs, such as, anaesthesiology drugs may cause damage to the peripheral veins. Thus, it is important where such drugs are injected into a peripheral vein, the injection should be delivered through the peripheral vein into the main blood pool of the patient as quickly as possible.

Another case in which it is essential that a discrete quantity of liquid be injected rapidly into a patient, is in the case of a bolus injection where a radionuclide liquid is injected intravenously and is directed to, for example, the heart or other organ to enable nuclear imaging or counting to be made. It is particularly important that the discrete quantity of radionuclide should be delivered to the heart with the minimum amount of mixing with the blood or the driving liquid used with the bolus. Where mixing takes place, it will be appreciated that the imaging or counting will be much less clear and the counting of lower statistical significance than where the fluid is retained in a discrete quantity.

In general, bolus injections are delivered by pushing the radionuclide liquid through the venous system with a driving liquid. A typical driving liquid is a saline solution. One way of doing this is to connect an intravenous needle to one port of a three-way valve. The other two ports are respectively connected to a syringe in which the bolus radionuclide liquid is stored, and a second syringe in which the driving liquid, generally saline solution, is stored. The valve is set initially so that the first syringe with the radionuclide is connected to the intravenous needle, and the radionuclide is dispensed from the syringe through the intravenous needle. The valve is then immediately switched over to connect the saline solution syringe to the intravenous needle, and the radionuclide is then flushed through the veins by delivering the saline solution rapidly from the syringe into the vein.

Unfortunately, this technique is cumbersome, and in general requires two people to operate it, one to operate the radionuclide syringe, and the other to operate the driving fluid syringe. Another very important problem that arises with this technique is that it is extremely difficult to have the saline solution following immediately after the radionuclide liquid, and thus mixing of the radionuclide with the blood occurs very often before the saline solution is delivered into the vein. Furthermore, it has been found in the past that using this technique also causes undesirable mixing between the radionuclide liquid and the saline solution. Thus, by the time the radionuclide is delivered to the organ which is being examined, in general the heart, it has mixed considerably with both the blood and the saline solution, and thereby accurate nuclear imaging cannot be achieved.

Another known device for delivering a bolus injection is disclosed in U.S. Pat. Specification No. 4,364,376. This device comprises a bolus retainer which is essentially a cylindrical member which forms a chamber in which the bolus liquid is stored. A needle is attached to one end and a valve is attached to the other end. A syringe is initially connected to the valve and the valve is opened to the bolus chamber. Radionuclide is then drawn into the bolus chamber, and the valve closed. A syringe is then filled with a driving liquid generally saline solution, and reconnected to the valve. The valve is then opened and the driving liquid is pumped into the bolus chamber, which in turn delivers the bolus and driving liquid into the patient's vein. The problem with this device is that the bolus chamber tends to be relatively long, and thus leads to a very cumbersome device. This is a particular problem, since it is generally necessary to shield the bolus chamber with a heavy lead radiation shield to protect the doctor or nurse from radiation. Thus, this is an extremely awkward device to handle, and because of this, can cause the needle to move around in the patient's arm, thereby causing considerable pain and discomfort, and in many instances can cause the needle to project right through the vein and into tissue. This, it will be appreciated, is a very serious problem. A further disadvantage of this device is that because of the construction of the bolus chamber, it has been found that considerable mixing of the bolus liquid and the driving liquid takes place in the chamber. Thus, by the time the radionuclide reaches the patient's heart it is well diluted and nuclear imaging is most inaccurate.

There is therefore a need for a device which overcomes the problem of known devices for delivering bolus injections, as well as known devices for delivering any discrete quantity of liquid into the body.

OBJECTS OF THE INVENTION

One object of the invention is to provide a device for storing a discrete quantity of liquid for use with a medical syringe, whereby the discrete quantity of liquid can be delivered into a vein or other part of the human body, with the minimum of mixing taking place between the discrete quantity of liquid and the blood, and where a driving fluid is used between the discrete quantity of liquid and the driving liquid. It is also an object of the invention to provide a device which is convenient and easy to use, and minimizes the risk of pain and discomfort to the patient during use. Another object of the invention is to provide a device which can be readily easily used. A further object of the invention is to provide a device which can be readily easily and relatively cheaply manufactured. A still further object of the invention is to provide a device which can be used for a bolus injection which minimizes the risk of mixing between the bolus liquid, the driving liquid and the patient's blood.

SUMMARY OF THE INVENTION

According to the invention, there is provided a device for storing a discrete quantity of liquid for use with a medical syringe, the device comprising a body member having a non-linear passageway to store the discrete quantity of liquid, and a pair of communicating means communicating respectively between the passageway and the syringe reservoir, and the passageway and a needle.

In one embodiment of the invention, the passageway is a tortuous passageway.

Preferably, the passageway is in the form of a helix.

In another embodiment of the invention, the passageway is of relatively small cross-sectional area.

In a further embodiment of the invention, the device comprises a body member which comprises a core member of circular cross-sectional area, and the passageway is formed by a helical groove formed around the periphery of the core member.

In another embodiment of the invention, a cylindrical member extends around the core member to close the helical groove.

Preferably, one communicating means is provided by a female connecting member extending from one end cap of the body member to engage a luer or record male connector extending from the syringe, and the other communicating means is provided by a male connecting member extending from the other end of the body member to engage a luer or record female connector of the needle, the male and female connecting members communicating with the helical groove.

Alternatively, the passageway is formed by a tube extending between the communicating means.

In another embodiment of the invention, the core member is adapted for mounting in the reservoir of a syringe intermediate the plunger and syringe outlet, the grooves being closed by the wall of the syringe and the inlet to the groove forming the communicating means with the syringe reservoir, and the outlet from the grooves forming the communicating means through the syringe outlet with the needle.

Advantageously, a radiation shield is provided to surround the body member and extends substantially the length of the body member.

In a further embodiment of the invention, the radiation shield is detachable from the body member, and is retained by a releasable clamping means.

Additionally, the invention provides a syringe incorporating the device.

Additionally, the invention provides a syringe comprising a primary reservoir and a primary plunger to discharge liquid from the primary reservoir, a secondary reservoir communicating with the primary reservoir and a secondary plunger in the secondary reservoir to draw up a small quantity of liquid.

According to a still further embodiment of the invention, the secondary reservoir is provided by a secondary syringe mounted in the primary plunger, the secondary syringe outlet extending axially into the primary reservoir.

In a still further embodiment of the invention, the secondary syringe is releasably mounted in the primary plunger.

Additionally, the invention provides a method for administering a discrete quantity of liquid intravenously using the syringe, the method comprising the steps of drawing a driving liquid into the primary reservoir by withdrawing the primary plunger, inserting the secondary syringe into the primary plunger so that the secondary reservoir of the secondary syringe communicates with the primary reservoir of the primary syringe, drawing in the discrete quantity of liquid into a passageway of a device communicating with the primary reservoir of the primary syringe by withdrawing the secondary plunger of the secondary syringe, removing the secondary syringe from the primary plunger, discharging the discrete quantity of liquid and the driving liquid by depressing the primary plunger of the primary syringe.

ADVANTAGES OF THE INVENTION

The advantages of the invention are many, and will be readily apparent to those skilled in the art. However, one important advantage of the invention is that it provides a device which is relatively short and compact, and not in any way cumbersome, and which can readily easily be used and held by a person administering the injection without any difficulty. A further advantage of the invention is that by virtue of the fact that the device can be easily held for administering an injection, the risk of pain and discomfort to the patient is almost completely eliminated. A further advantage of the invention is that by virtue of the fact that the device is easily handled, there is virtually no risk of a needle used with the device, passing through the vein and out into tissue of the patient. A very important advantage of the invention is that by virtue of the fact that the liquid passageway is provided by a relatively small bore, the chance of the discrete quantity of liquid mixing with either the patient's blood or driving liquid which may be used to deliver the discrete quantity of liquid into the patient, is greatly reduced. Furthermore, by virtue of the fact that the device is provided with a helical passageway, a relatively easily manufactured, constructed and used device is provided.

These objects and advantages of the invention will be readily apparent to those skilled in the art from the following description of some preferred embodiments thereof, given by way of example only, with reference to the accompanying drawings.

DETAILED DESCRIPTION OF THE INVENTION

Referring to the drawings, and initially to FIGS. 1 to 5, there is provided a device according to the invention, indicated generally by the reference numeral 1, for use with a medical syringe 2 and needle 3, for storing a discrete quantity of fluid for injection into the body. In this case, the device 1 is ideally suited for administering a bolus injection. Before describing the device, the syringe and needle will first be described. The syringe 2 comprises a barrel 4 which forms a reservoir 5. A plunger 6 delivers liquid from the reservoir 5. The needle comprises a hub 7 of plastics material with a stainless steel cannula 8 having a pointed tip 9 extending from the hub 7.

The device 1 comprises a body member 10 having a core member 11 of plastics material surrounded by a cylindrical sleeve 12 of clear plastics material. A nonlinear tortuous liquid path for storing the bolus liquid is provided by a helical groove 15 formed around the periphery of the core member 11. The sleeve 12 forms a seal around the periphery of the core member 11, thereby preventing fluid leaks between adjacent turns of the helical groove 15. Communicating means to connect the groove 15 to the syringe and needle, are provided by female and male connector members 17 and 18, respectively, extending from the ends of the core member 11. Both members 17 and 18 are connected to the groove 15 by axial bores 19 which extend through the connector members into the core member 11, and lateral bores 20, which extend transversely across the core member to connect the axial bores 19 to the ends of the groove 15. The female connector member 17 is of plastics material, and is moulded integrally with the core member, and is provided with a luer recess 21 to engage a corresponding male luer connector 22 on the syringe 2. The male connecter member 18 also of plastics material and moulded integrally with the core member, has an external luer taper 23 to engage a female taper 24 of the hub 7 of the needle 3.

A radiation shield 27 to protect the person administering the injection, is releasably mounted on the device 1. The shield 27 comprises a thick-walled barrel 28 of lead. An inspection glass 29 is provided in the barrel 28, to permit the user to see the liquid in the groove 15. The glass is a heavy lead impregnated glass. The barrel 28 is secured to the body member 10 by a compressible washer 30 mounted in an annular groove 31 at the end of the barrel 28. The compressible washer 30 is compressed by a threaded end cap 32 which engages threads 33 on the barrel 28. On tightening, the end cap 32 acts on a steel washer 34 which bears against the compressible washer 30, thereby squeezing or clamping the washer in a radial direction to engage the cylindrical sleeve 12 of the device 1. To assist a user, finger grips 35 are provided on the side of the end cap 32.

In use, the device 1 is attached to the syringe 2 and needle 3. The needle is immersed in a saline solution, which is drawn through the needle, and in turn through the helical groove 15, and into the reservoir 5 of the syringe 2. When a sufficient quantity of saline solution has been drawn into the syringe 2, usually when the syringe is just about full of saline solution, the needle 3 is then immersed in the radionuclide for the bolus injection. This is usually carried out behind a protective screen, or in a protected preparation area. The required amount of radionuclide is then drawn in through the needle, and into the helical groove 15 of the device 1. The quantity of bolus fluid drawn into the device 1 can readily easily be measured by counting the number of turns of the groove filled with the bolus. Each turn corresponds to a specific volume of fluid. Verification that the correct quantity of radionuclide has been drawn up is obtained by placing the device into a radiation measuring device. The radiation shield 27 is then fitted in place and the device removed from behind the screen. The device is then ready for use. The needle is inserted into a vein in the arm or any other suitable position of a patient, and by rapidly depressing the plunger 6 of the syringe 2, the bolus is administered to the patient, and the saline solution rapidly drives the bolus to the desired location, normally the heart, to permit a radiation scan of the heart to be made.

Figure 1:
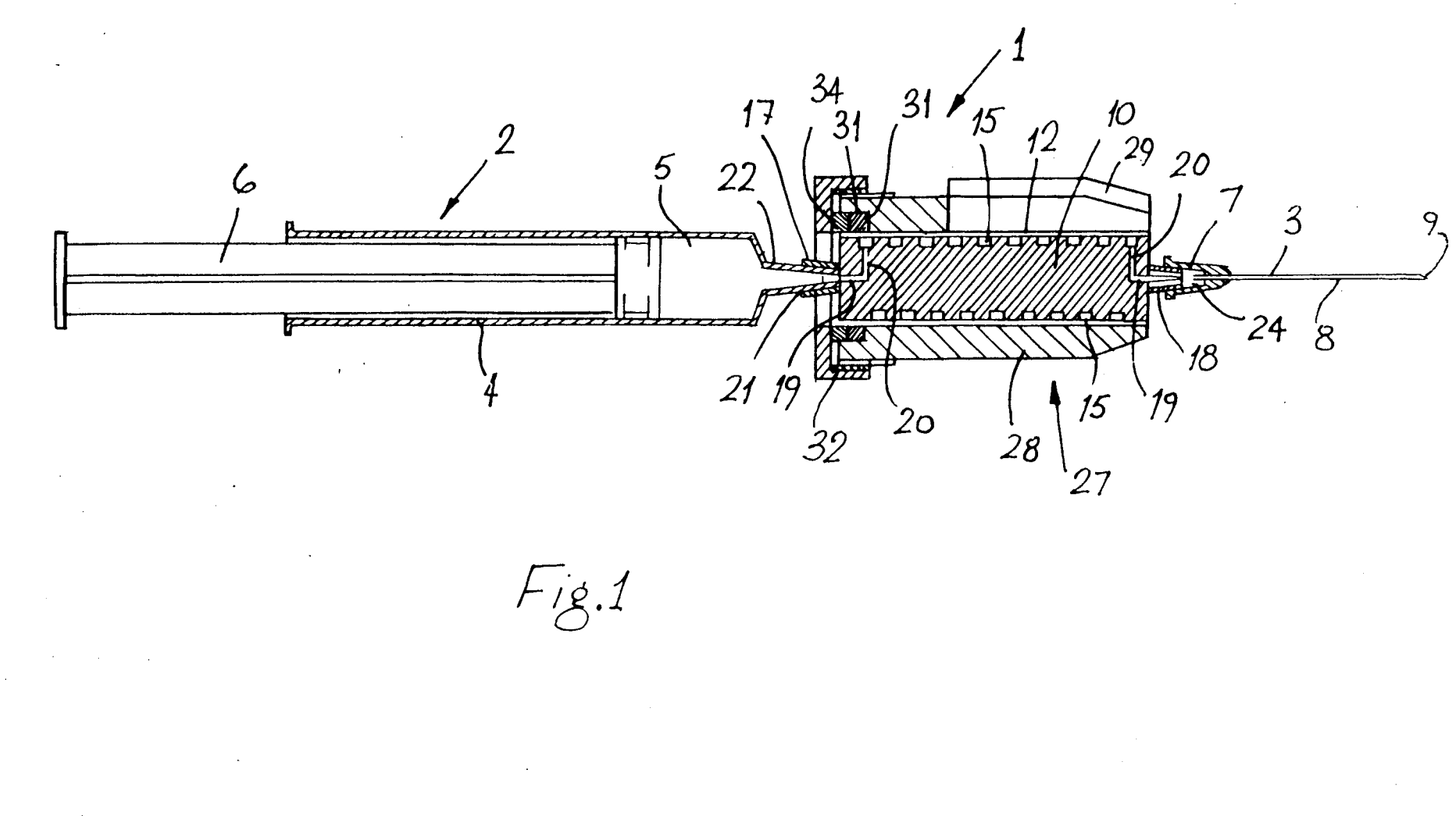
FIG. 1 is a sectional view of a device according to the invention, illustrated mounted on a medical syringe and needle.
Figure 2:
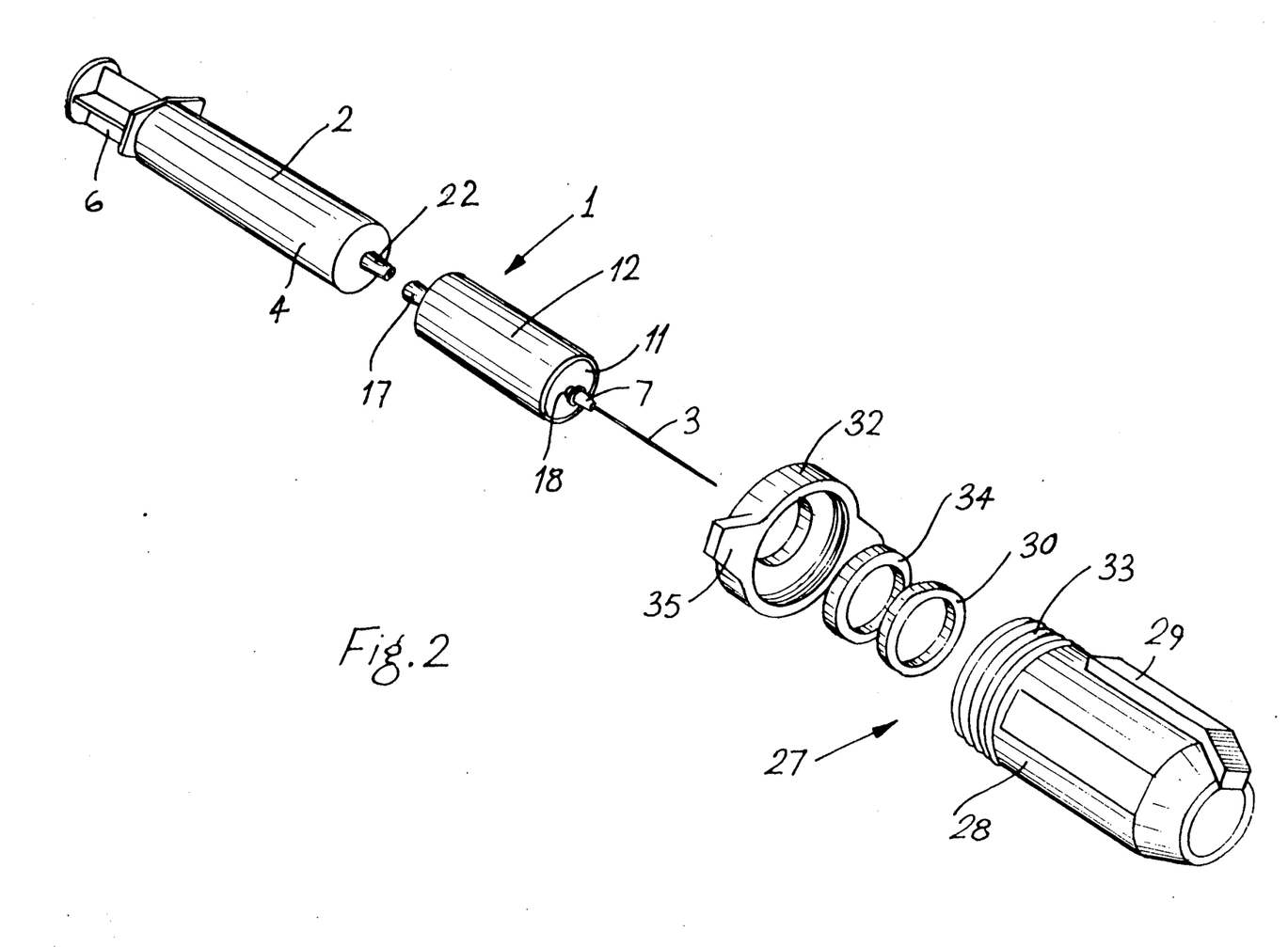
FIG. 2 is an exploded view of the device of FIG. 1.
Figures 3, 4, 5:
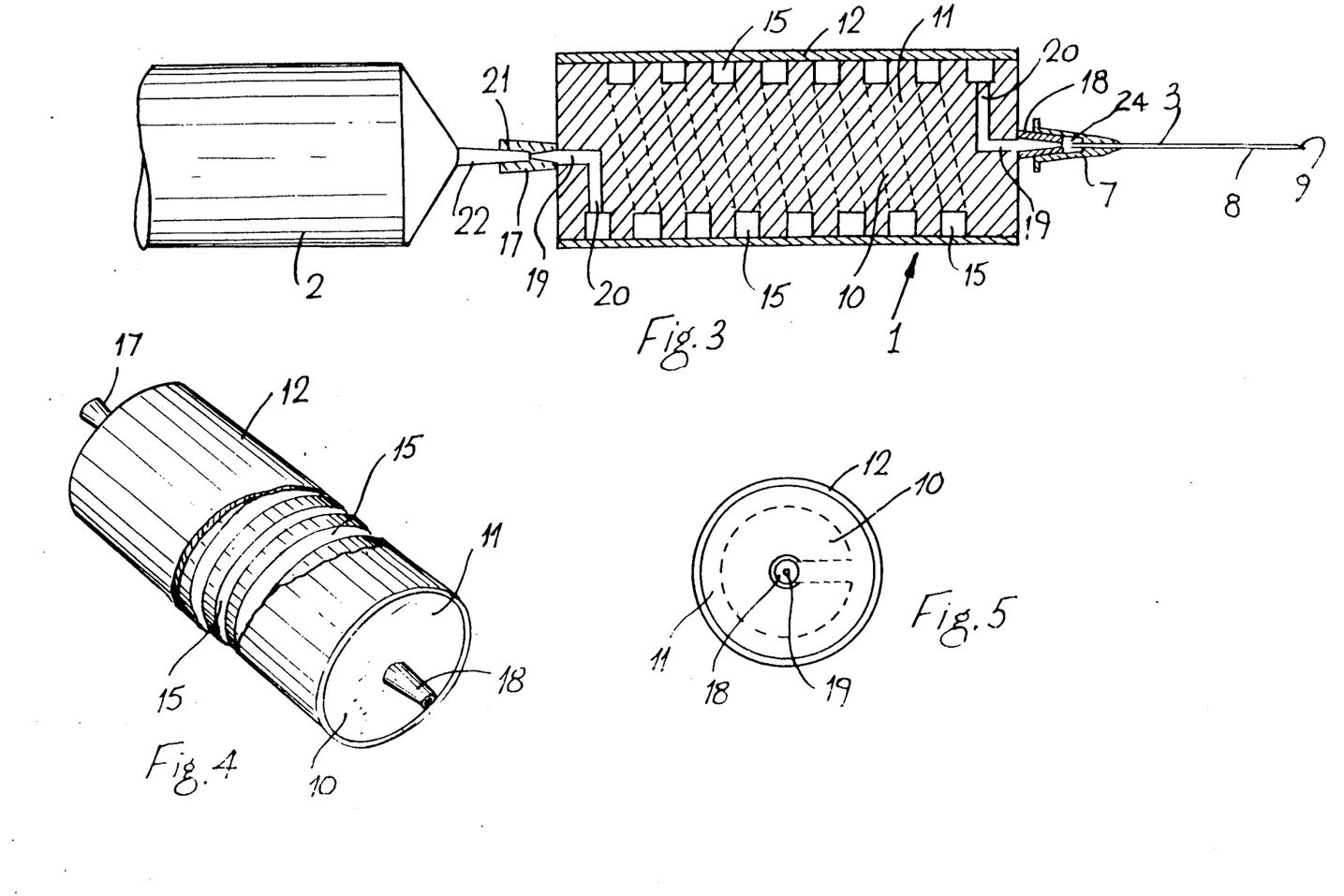
FIG. 3 is a detailed cross-sectional view of the device of FIG. 1.
FIG. 4 is a perspective view of a portion of the device of FIG. 1.
FIG. 5 is an end view of portion of the device of FIG. 1.

In certain cases it may be preferable between drawing in the saline solution and the bolus liquid, to draw in a small quantity of air to act as a barrier in the groove 15 between the saline solution and the bolus liquid. Additionally, when the desired quantity of bolus has been drawn in, it may also in certain cases by advantageous to draw in a further small quantity of air to act as a barrier between the patient's blood and the bolus fluid. By virtue of the fact that the boundary between the bolus liquid and saline solution is in the groove 15 of the device 1, mixing between the saline solution and the bolus does not occur. Indeed, where a small quantity of air is drawn in as a barrier between the two, this further avoids mixing of the two liquids. Furthermore, by virtue of the fact that mixing of the bolus fluid and the driving fluid, namely, the saline solution, is avoided in the device 1, the only mixing that can occur will be subsequently in the vein of the patient. Since the bolus is normally driven rapidly along the vein, the amount of mixing between the saline solution and the bolus is thus minimized. It has been found in devices known heretofore that considerable mixing between the bolus and driving fluid took place. Additionally, by virtue of the fact that the bolus is retained in a small discrete volume in the device, this also assists in avoiding subsequent mixing of the bolus with the patient's blood.

It has also been found that by drawing in a further small, second quantity of saline solution into the groove 15 of the device 1 after the bolus liquid has been drawn in, the second quantity of saline solution acts as a buffer between the patient's blood and the radionuclide in use. By virtue of the fact that the radionuclide is trapped between the saline solution, in other words, a small quantity of saline solution is provided at the beginning of the radionuclide, and the large driving quantity of saline solution is provided at the end, the radionuclide remains substantially in one homogeneous quantity, and does not disperse and mix with the patient's blood. Thus, it will be appreciated that when the radionuclide reaches the heart it will still be in a discrete quantity, and will then fill the chambers of the heart or other organ being examined, thereby permitting active radionuclide imaging or other imaging of the heart or other organ. In fact, it will be appreciated that if desired small quantities of air may be provided between the two quantities of saline solution and the radionuclide. This, it is envisaged, will further avoid mixing of the radionuclide with the saline solution.

A further and very important advantage of the invention, is that by virtue of the fact that the liquid path is tortuous, in other words, in this case formed by a helical groove, the device is short and compact. One of the problems with devices known heretofore is that the length of the device was far too long to allow easy manipulation of the device by the person administering the bolus, particularly if a radiation shield was used on the device.

Figure 6:
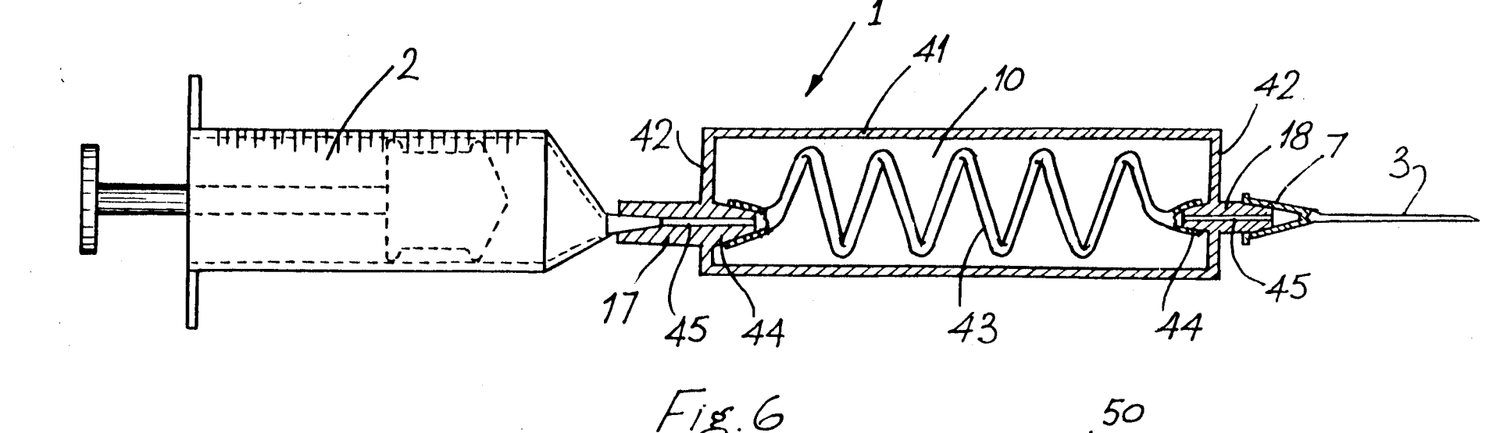
FIG. 6 is a sectional view of the device according to another embodiment of the invention, illustrated mounted on a syringe and needle.

Referring now to FIG. 6, there is illustrated a device 40 according to another embodiment of the invention. In this case, the device 40 is somewhat similar to the device just described, and similar components are identified by the same reference numerals. In this case the body member 10 is provided by a cylindrical sleeve 41 of clear plastics material closed by end caps 42. In this case, the tortuous liquid path is formed by an elongated small bore tube 43 wound in the form of a helix. The female and male connectors 17 and 18 both terminate internally in the end caps 42 in connectors 44, which engage the ends of the tube 43. Bores 45 through the connectors 17 and 18, form a communicating means between the syringe 2 and the needle 3.

Although not illustrated, this device may similarly be shielded by the radiation shield 27.

The use of this device is similar to that already described.

Figure 7:
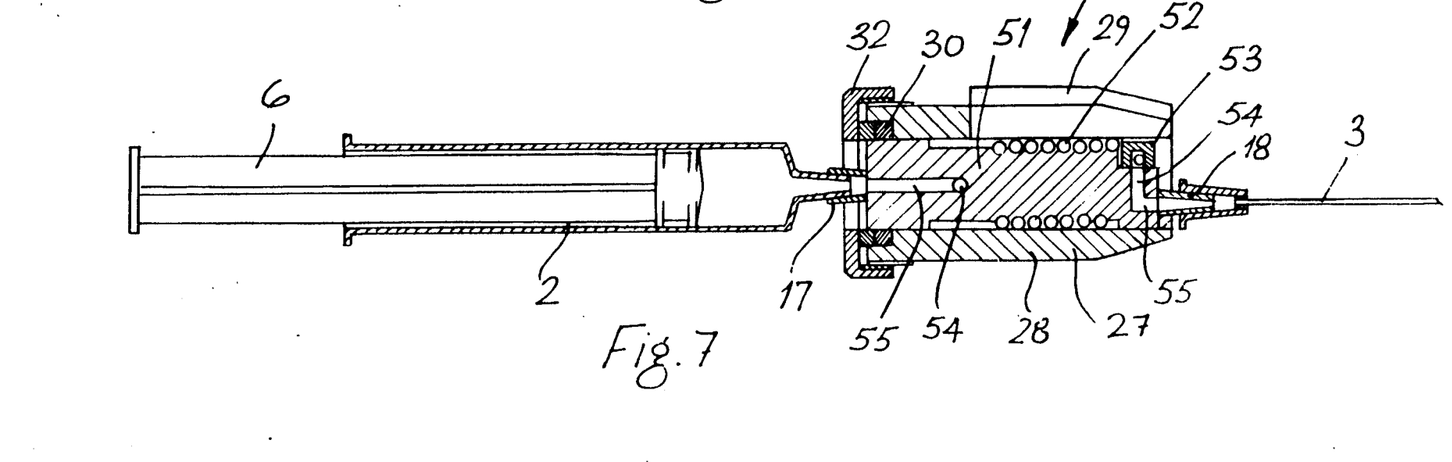
FIG. 7 is a sectional view similar to FIG. 1 of a device according to another embodiment of the invention.
Figure 8:
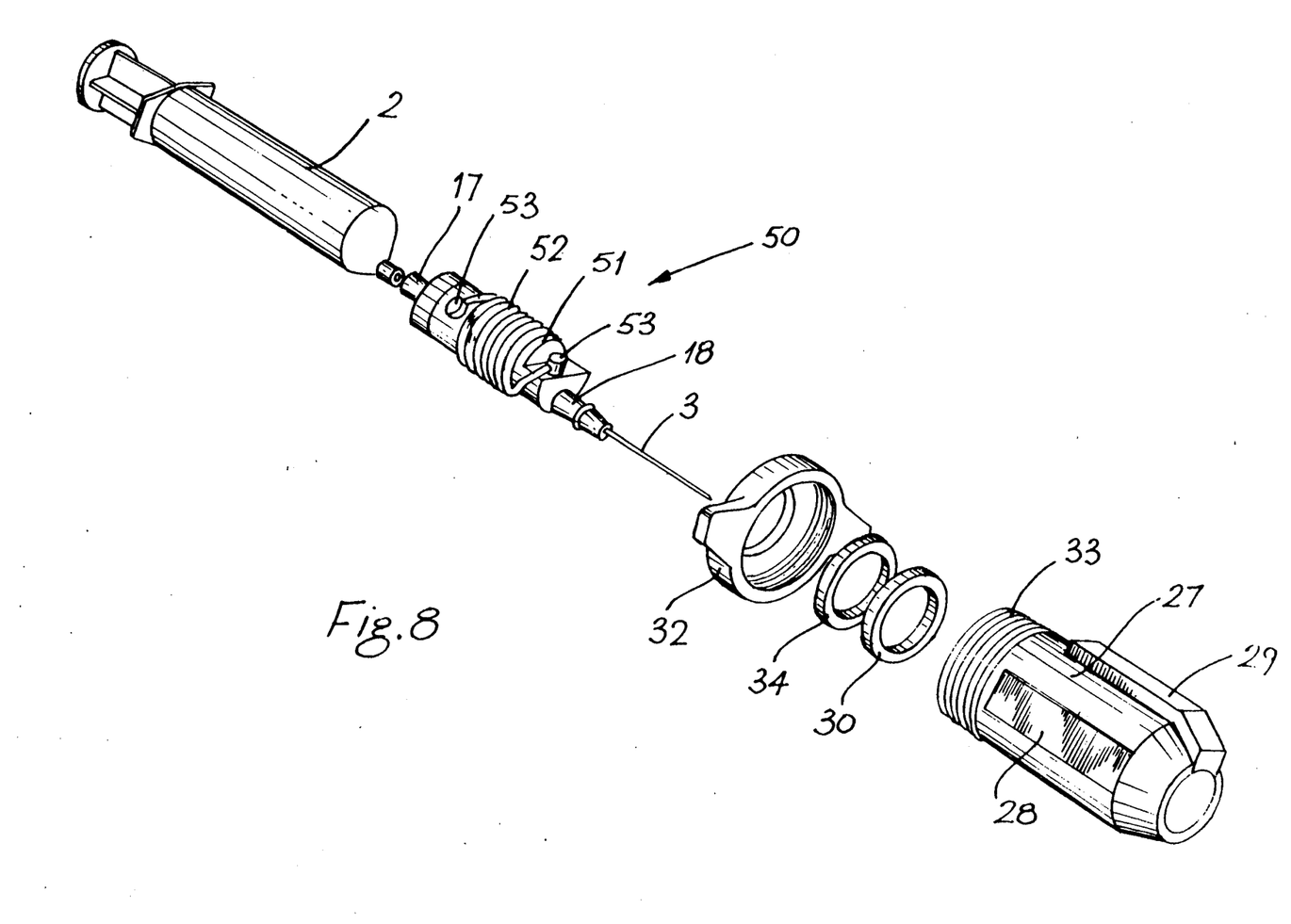
FIG. 8 is an exploded view of the device of FIG. 7.

Referring now to FIGS. 7 and 8, there is illustrated a device 50 according to another embodiment of the invention. This device is somewhat similar to that described with reference to FIGS. 1 to 5, and similar components are identified by the same reference numerals. In this case, the body member is provided by a core member 51, around which a small bore tube 52 is wound in the form of a helix to provide the liquid path. The ends of the tube 52 terminate in plugs 53 which connect the ends of the tube through bores 54 and 55 in the core member 51, to connector members 17 and 18 for connecting the device respectively to the syringe 2 and needle 3. The device 1 is protected by a radiation shield 27 similar to the shield 27 of the device of FIGS. 1 to 5, and the compressible washer 30 bears on the core member 51 to retain the shield in place on the body member.

The use of this device is similar to those just described.

Figure 9:
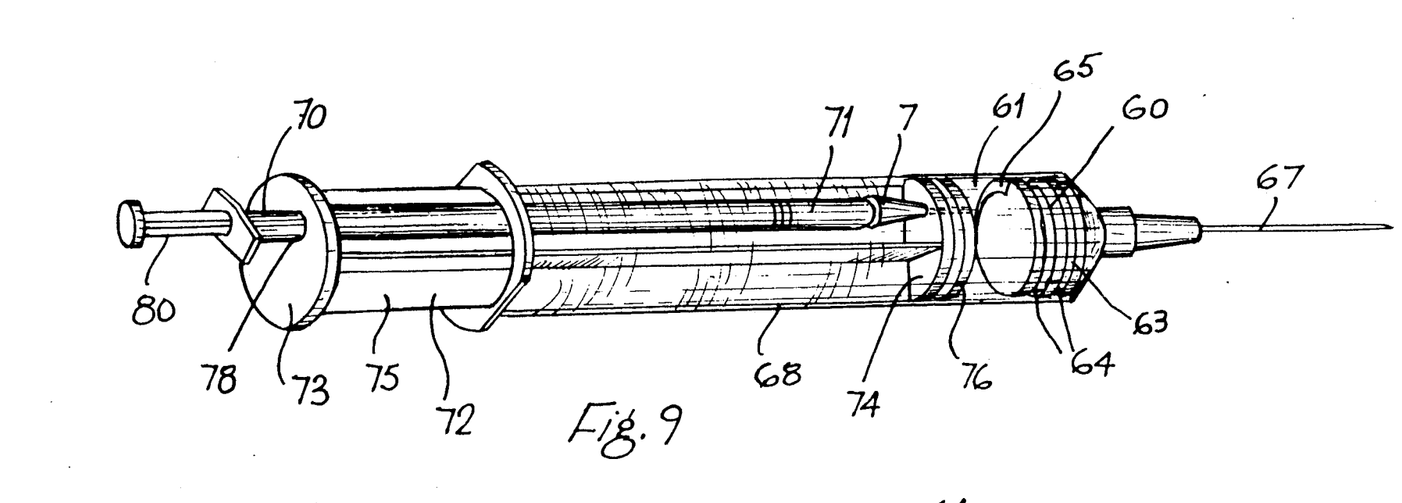
FIG. 9 is a perspective view of a device according to another embodiment of the invention.
Figure 10:
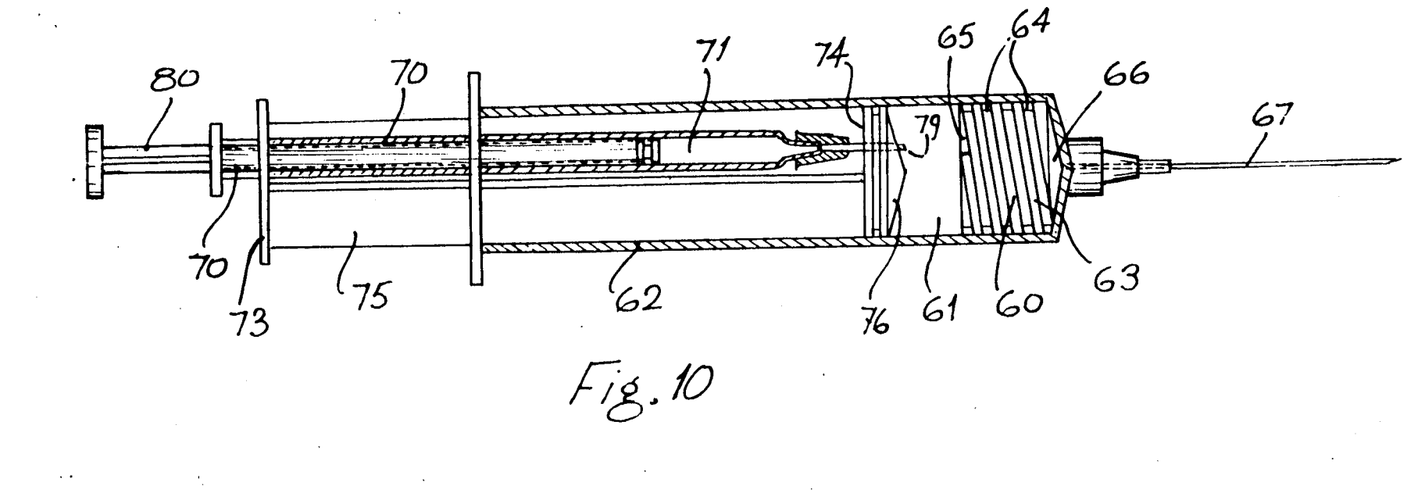
FIG. 10 is a sectional view of the device of FIG. 9.

Referring now to FIGS. 9 and 10, there is illustrated a device 60 according to another embodiment of the invention. In this case, the device 60 is mounted in the reservoir 61 of a syringe 62 also according to the invention. The syringe 62 will be described in detail below. The device 60 comprises a body member, in this case formed by a core member 63. The liquid path is formed by a helical groove 64 on the periphery of the core member 63. The arrangement of the groove 64 and the core member 63 is substantially similar to the core member 11 of the embodiment of the invention described with reference to FIGS. 1 to 5. The core member 63 is a tight fit in the reservoir 61 and the barrel wall 68 of the syringe 62, closes the groove 64 and ensures that leakage will not take place between adjacent turns of the helical groove 64. An inlet 65 to the groove 64 forms a communicating means between the groove 64 and the reservoir 61. An outlet 66 from the groove 64 forms a communicating means between the groove 64 and a needle 67 on the syringe 62.

In this case, the syringe 62 is essentially a primary syringe which forms the primary reservoir 61. A secondary syringe 70 forming a secondary reservoir 71, is mounted in a primary plunger 72 of the primary syringe 62. The diameter of the secondary syringe is less than that of the primary syringe. The secondary syringe 70 permits small volumes of liquid to be accurately and sensitively drawn into either the syringe or the helical groove 64 of the device 60. The primary plunger 72 comprises a top plate or disc 73 and bottom disc 74 joined by four longitudinal ribs 75, all of plastics material moulded integrally. A stopper 76 mounted on the bottom disc 74 sealably engages the barrel wall 68 for drawing in and pumping out liquid from the primary reservoir 61. A hole 78 is provided in the top disc 73 to accommodate the secondary syringe 70. A short needle 79 on the secondary syringe 70 extends through the bottom disc 74 and the stopper 76, to communicate with the primary reservoir 61. The secondary syringe 70 is thus secured in the primary plunger 72. A secondary plunger 80 is provided in the secondary syringe 70.

In use, when the syringe 62 and device 60 are for use in delivering a bolus injection, the needle 67 of the primary syringe 62 is immersed in a saline solution, and the primary plunger 72 is withdrawn to draw saline solution through the groove 64 of the device 60 into the primary reservoir 61, thus substantially filling the primary reservoir 61 with the desired quantity of saline solution. During this operation, the secondary plunger 80 is in the depressed position. The needle is then immersed in the radionuclide bolus solution, and the desired amount of radionuclide is withdrawn into the groove 64 of the device 60 by withdrawing the plunger 60 of the secondary syringe 70. Because of the fact that the secondary syringe is of considerably smaller bore than the primary syringe, the radionuclide liquid can be drawn in much more accurately and sensitively than if one were to draw it in using the primary plunger of the primary syringe. If desired, a further small quantity of saline solution may be drawn in by the secondary plunger to act as a buffer between the radionuclide and the patient's blood.

The syringe and device 60 is then ready for administering the bolus to a patient. The needle 67 is inserted in the vein of the arm or any other suitable vein of the patient, and the primary plunger 72 and secondary plunger 80 are rapidly depressed, thereby rapidly delivering the radionuclide into the vein of the patient.

The advantage of having the secondary syringe is that it leads to an extremely sensitive apparatus. It permits the radionuclide to be drawn into the liquid path of the device with precision. This is because of the fact that the secondary syringe has a relatively narrow diameter. In fact, it will be appreciated that the narrower the diameter of the secondary syringe, the more sensitive the device will be.

Although not illustrated, a radiation shield may be provided around the outer lower portion of the syringe barrel adjacent the device 60, to reduce radiation exposure to a doctor or nurse delivering the injection. A radiation shield substantially similar to that described with reference to FIGS. 1 to 5, could be used. The radiation shield would be fitted to the syringe after the radionuclide had been drawn into the device 60. Indeed, in certain cases it is envisaged that if desired the radiation shield could extend over the entire length of the primary syringe, although it is felt that this should not be necessary, since the radionuclide is retained in the device 60.

Figure 11:
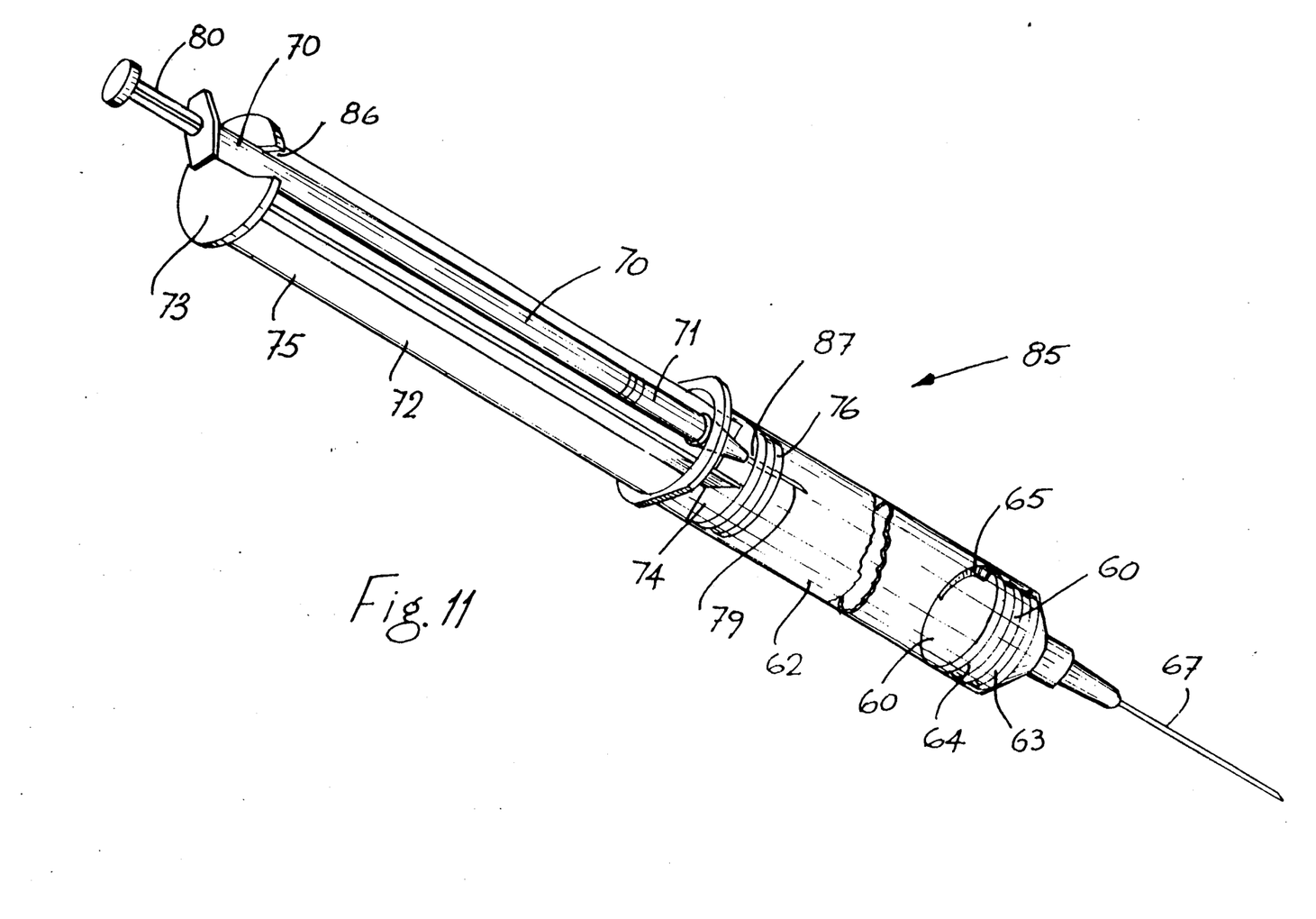
FIG. 11 is a view similar to FIG. 9 of a device according to another embodiment of the invention.

Referring now to FIG. 11, there is illustrated a syringe 85, also according to the invention, and a device 60 mounted in the syringe 85. The syringe 85 and device 60 are substantially similar to those just described with reference to FIGS. 9 and 10, and similar components are identified by the same reference numerals. The main difference between the syringe 85 and the syringe of FIGS. 9 and 10, is that the secondary syringe 70 is releasably mounted in the primary plunger 72 of the primary syringe 85. In this case, a slot 86 is provided in the top disc member 73 to releasably engage the barrel of the secondary syringe 70. Pips (not shown) are provided in the slot 86 so that the secondary syringe 70 is engagable with snap-fit action. A hole 87 is provided in the bottom disc 74 to accommodate the needle 79 of the secondary syringe.

In use, it is envisaged that the primary and secondary syringes 85 and 70, will be sold disassembled. To draw up the saline solution, the primary plunger 72 without the secondary syringe 70 mounted, is withdrawn and saline solution is drawn into the primary reservoir 61. When the desired amount of saline solution has been drawn in, the secondary syringe 70 is then mounted in the primary plunger. The needle is aligned with the hole 87, and the syringe barrel is engaged in the slot 86. The secondary syringe 70 is then pressed downwards in the primary plunger 72, so that the needle 79 punctures the stopper 76 of the primary plunger 72, thus the secondary reservoir 71 of the secondary syringe 70 communicates with the primary reservoir 61. The secondary plunger 80 is then withdrawn to draw in the desired amount of radionuclide into the liquid passageway 64 of the device 60. When the desired amount of radionuclide has been drawn in, the secondary syringe 70 is then removed from the primary plunger 72 and the syringe 85 is then ready for injecting the patient. To dispense the radionuclide and driving liquid into the venous system, the primary plunger 72 is rapidly depressed, thereby dispensing the radionuclide and the saline solution. By virtue of the fact that the stopper of the primary plunger is of a relatively resilient material, it is effectively self-sealing, and thus reseals the small puncture made by the secondary needle 79 of the secondary syringe 70.

The advantage of having the secondary syringe disposable is that it in many cases makes the syringe more easily handleable.

It will also be appreciated that while the secondary reservoir and syringe have been described as being mounted in the plunger of the primary syringe, this is not necessary. In certain cases, it is envisaged that the secondary syringe may be mounted externally of the primary syringe. Indeed, it is envisaged in other cases that the secondary syringe may in fact form the plunger of the primary syringe, and the reservoir of the secondary syringe would communicate with the reservoir of the primary syringe through a small bore in the stopper of the primary plunger.

It will also be appreciated that while particular configurations and shapes of devices have been described, any other suitable shape or configuration could be used. For example, it is envisaged that the liquid passageway may be formed by means other than a helical groove or a small bore tube wound in the form of a helix. For example, the liquid path could be formed by a plurality of longitudinal bores extending through the body member, and pairs of bores being joined at their ends to form one long bore doubling backwards and forwards on itself. Further, the liquid path could be formed by a tube wound up in any convoluted or tortuous or non-linear arrangement in the body member. In fact, in certain cases, the tube could be provided on a body member formed by a framework or any other suitable support means.

It will of course be appreciated that the cross-sectional area of the liquid path may be any suitable or desired cross-sectional area. It has been found in use that if the cross-sectional area is in the range of 1.76 sq. mm to 5 sq. mm, particularly advantageous results have been achieved. However, it will be appreciated that the cross-sectional area of the liquid path could be greater or lesser than these given areas.

Of course, it will be appreciated that while the liquid passageway has been described as being formed by the bore of a tube or a groove, any other suitable means of forming a liquid passageway could be used without departing from the scope of the invention.

While in all the embodiments of the invention just described, the driving saline solution has been described as being drawn into the reservoir through the device, this is not necessary, and in certain cases it is envisaged that the saline solution may be drawn directly into the syringe and the device could then be mounted on the syringe and the small quantity of radionuclide could be drawn into the liquid path of the respective device by further withdrawing the plunger of the syringe, or in the case of the device of FIGS. 9 and 10 by withdrawing the secondary plunger.

In most cases it will be appreciated that the quantity of radionuclide drawn into the liquid passageway of the device can be measured either by measuring the amount the plunger has been withdrawn while drawing in the radionuclide or by counting the number of turns of the liquid passageway filled with the radionuclide. Usually the activity of the radionuclide will be checked by placing the syringe and device in a radiation dose calibrator.

It has been found that a particularly important advantage of the invention is that by virtue of the fact that the device of the various embodiments of the invention is relatively short, and as already described, this results from the fact that the liquid path is formed by many turns of a helix, the device is particularly adaptable and easy to use. Furthermore, by virtue of the fact that the device is relatively short, a relatively robust device is provided. Thus, a bolus injection can be administered readily easily with minimal discomfort and pain to the patient. Furthermore, and most importantly, the fact that the device is relatively short and maneuverable allows it to be easily shielded, thus increasing radiation safety to the technician or person administering the dose.

It is envisaged that while in the embodiments of the invention described the device and syringe have been manufactured from plastics material, and in general, of clear plastics material moulded, any other suitable material or forms of construction could be used. In fact, the helical groove could be either machined into the core member or could be formed during moulding of the core member. It will of course be appreciated that materials other than plastics material could be used for the core member.

It will also be appreciated that while the radiation shield has been described in most embodiments of the invention as merely covering the device for storing the radionuclide, the radiation shield could, if desired, extend to cover both the syringe and the device, and in certain cases could extend further to cover at least portion of the needle. It will also of course be appreciated that radiation shields other than that described could be used. In certain cases it is envisaged that the radiation shield may be a fixed structure on the device, and it may not be releasable. Further, it is envisaged that the device according to the invention for storing the radionuclide, has been described as being mounted on a needle and a syringe, this is not necessary, the device in many cases may be manufactured and sold on its own without a syringe and needle. Further, it is envisaged in certain cases that the device may be preloaded with a radionuclide and sold with the radionuclide already preloaded. Furthermore, it will be appreciated that while in various embodiments of the invention, the method of drawing the radionuclide into the syringe has been described in certain cases with airlocks between the saline solution, this is not necessary, the radionuclide may be drawn in without having an airlock or airlocks as the case may be, between the radionuclide and the saline solution. Additionally, it will of course be appreciated that it is not necessary for a second quantity of saline solution to be drawn into the device to act as a buffer between the radionuclide and the blood. Needless to say, any other driving solution besides a saline solution, could be used.

It is also envisaged that while the device has been described for use in a bolus injection, in other words, for storing and delivering a small quantity of radionuclide, the device could be used for any other purpose. It could be used for delivering a small discrete quantity of any type of liquid to a patient, either through the venous system or any other system. The small quantity of liquid could be driven by any suitable driving fluid. In general, however, it is envisaged that the driving liquid would be inert. Alternatively, the device could be used to deliver two or more liquids side by side with minimal mixing. A further important advantage of the device is that it permits a liquid, for example, a toxic drug, to be delivered rapidly through the vein and into the general systemic circulation. This will be particularly beneficial where it is important to get the drug quickly into the blood pool and major blood vessels and/or organs, and away from the peripheral veins of the arm or other injection sight where the elements of the drug might lodge and cause toxic effects in the vein, or not be delivered fully, and thus not achieve maximum impact. It is well known that there are drugs which are locally toxic to peripheral veins, and thus, it would be essential to deliver the drug rapidly into the blood pool and major blood vessels or organs away from such peripheral veins. It will be appreciated that the present device can achieve this readily easily. Such drugs which may cause problems to peripheral veins are, for example, used in chemotherapy and also certain antibiotics. Indeed, in certain cases with antibiotics it has been found that only three injections may be given into a vein before the vein becomes useless for drug administration, due to the action of the drugs on the vein. However, by using the present invention the drug can be quickly flushed through the vein and the driving fluid, as well as having a flushing effect also may have a cleaning effect on the vein, thereby removing any traces of the drug in the vein into which the drug has been administered.

Furthermore, the device may be advantageously used for delivering a small dose of an active drug of less than the capacity of the device, for example, one millimeter dose. It will of course be appreciated that it is not necessary to fill the liquid passageway of the device with the discrete quantity of liquid being administered. In many cases, only a few turns of the helix may be filled, indeed, in certain cases it is envisaged that only one, and indeed maybe less than one turn may be filled with the liquid being administered to the patient. Furthermore, as the secondary syringe allows small quantities of a drug to be drawn in precise quantities into the device, and the driving solution ensures total delivery of the dosage, it has the further advantage that in virtually all cases where the device is used, the entire quantity of the discrete quantity of liquid, whether it is a drug, radionuclide or the like, will be delivered to the patient. Even where small residual amounts adhere as a result of surface tension to the wall of the liquid passageway, the driving liquid will remove any remaining traces of the drug, radionuclide or the like, and will accordingly deliver them into the patient's venous system. This, it will be appreciated, has considerable advantages over devices known heretofore, where in many cases, even using the smallest syringe, small quantities of a drug will be retained in the syringe, needle, and may even adhere to the plunger. This is a particular disadvantage when relatively small quantities of the drug or other liquid are being administered, as any residual amount of the drug or liquid remaining in the syringe will have a relatively large effect on the overall dose administered to the patient, and in many cases this may have extremely serious effects on the patient.

Additionally, it will be appreciated that while the shield has been described as being of lead, any other high density metal, or other high density material could be used. Furthermore, other glass could be used, besides that described.

While the driving liquid has been described in all the embodiments of the invention as a saline solution, any other suitable driving liquid could be used. In general, it is envisaged that it will be an inert solution.

Additionally, it is envisaged that while the syringes which have been described with reference to FIGS. 9 to 11, have been described as incorporating the device in the primary reservoir, this is not necessary. These syringes could be used without the device mounted in the primary reservoir, in which case it is envisaged that the device would be externally mounted, as described, for example, with reference to FIGS. 1 to 5. In other words, the syringe of any of FIGS. 9 to 11 could be used with any of the devices of the earlier FIGURES.

It will also of course be appreciated that while the device which is illustrated mounted in the syringes of FIG. 9 and 11, has been described as having a liquid passageway provided by a helical groove, the passageway could be provided by any other non-linear passageway, whether a convoluted, tortuous, or any other suitable construction.

While the device and syringe have been described with a needle attached, it will be appreciated that any other means for injecting into a patient's vein could be used, for example, a scalp vein set, or a butterfly, which in general would include a needle and tube, or indeed any other means could be used.

I claim:
1. A bolus syringe comprising:
    a housing having a bore therein forming a reservoir for storing a driving fluid means for driving a bolus liquid, and having an outlet therefrom,
    a plunger mounted in the reservoir and movable in first and second directions through the reservoir for respectively drawing in and discharging fluid from the reservoir through the syringe outlet,
    a body member mounted within a portion of the reservoir adjacent the syringe outlet, between the syringe outlet and the plunger, the outer cross sectional area of the body member defining the outer cross sectional area of the bore forming the reservoir, the body member having a single elongated non-branched tortuous passageway comprising means for storing the bolus liquid and some of the driving fluid and said passageway being of relatively small bore to minimize mixing of the bolus liquid and the driving fluid at an interface of the bolus liquid and the driving fluid, an inlet being provided adjacent one end of the body member for communicating the tortuous passageway with the reservoir and an outlet being provided adjacent the other end of the body member for communicating the tortuous passageway with the syringe outlet, so that in response to movement of the plunger in the first direction driving fluid is drawn into another portion of the reservoir through the tortuous passageway and the bolus liquid is drawn into the tortuous passageway, and in response to movement of the plunger in the second direction, first the bolus liquid and then the driving fluid are discharged through the syringe outlet.

2. A syringe as claimed in claim 1 in which a receiving means extends from the housing for receiving a needle, the syringe outlet being formed in the receiving means.

3. A syringe as claimed in claim 2 in which the body member is formed by a core member having a periphery and the passageway is formed by a groove formed around the periphery of the core member, wherein the housing encloses the groove.

4. A syringe as claimed in claim 3 in which the groove is a helical groove.

5. A bolus syringe comprising:
a primary housing having a bore therein forming a primary reservoir for storing a driving fluid means for driving a bolus liquid, and having an outlet therefrom,
a primary plunger mounted in the primary reservoir and movable in first and second directions through the primary reservoir for drawing fluid into the primary reservoir, and for discharging fluid from the primary reservoir, respectively,
a secondary housing having a secondary reservoir formed therein, and means for communicating the secondary reservoir with the primary reservoir, a secondary plunger movable in third and fourth directions through the secondary reservoir for drawing fluid into the secondary reservoir from the primary reservoir, and for discharging fluid from the secondary reservoir to the primary reservoir, respectively, and a body member mounted within a portion of the primary reservoir adjacent the outlet of the primary reservoir and between the primary plunger and the outlet from the primary reservoir, the outer cross sectional area of the body member defining the outer cross sectional area of the bore forming the primary reservoir, the body member having a single elongated non-branched tortuous passageway comprising means for storing the bolus liquid and some of the driving fluid and said passageway being of relatively small bore to minimize mixing of the bolus liquid with the driving fluid at an interface of the bolus liquid and the driving fluid, an inlet being provided adjacent one end of the body member for communicating the tortuous passageway with the primary reservoir and an outlet being provided adjacent the other end of the body member for communicating the tortuous passageway with the outlet from the primary reservoir, so that in response to movement of the primary plunger in the first direction driving fluid is drawn into the primary reservoir through the tortuous passageway and the bolus liquid is drawn into the tortuous passageway, and in response to movement of the primary plunger in the second direction the bolus liquid and the driving fluid are discharged through the outlet from the primary reservoir.

6. A syringe as claimed in claim 5 in which the body member is formed by a core member having a periphery and the passageway is formed by a groove formed around the periphery of the core member, wherein the primary housing encloses the groove.

7. A syringe as claimed in claim 5 in which means for receiving a needle extends from the primary housing and the primary reservoir outlet extends through the receiving means.

8. A syringe as claimed in claim 5 in which the secondary housing is formed by a secondary syringe, the secondary syringe being mounted in the primary plunger, wherein the means for communicating the secondary reservoir with the primary reservoir is disposed so as to extend through the primary plunger.

9. A syringe as claimed in claim 8 in which the secondary syringe is releasably mounted in the primary plunger.

* * * * *